United States Patent [19]
Zygmunt et al.

[11] Patent Number: 6,143,902
[45] Date of Patent: Nov. 7, 2000

[54] C-2 HYDROXYL PROTECTED-N-ACYL (2R, 3S)-3-PHENYLISOSERINE N-IMIDO ACTIVATED ESTERS AND METHOD FOR PRODUCTION THEREOF

[75] Inventors: Jan Zygmunt; James D. McChesney; Madhavi C. Chander, all of Boulder, Colo.

[73] Assignee: NaPro BioTherapeutics, Inc., Boulder, Colo.

[21] Appl. No.: 09/336,962

[22] Filed: Jun. 21, 1999

[51] Int. Cl.⁷ ............... C07D 207/40; C07D 207/444; C07D 209/56; C07D 209/34
[52] U.S. Cl. ............ 548/435; 548/486; 548/545; 548/548
[58] Field of Search ................... 548/435, 486, 548/545, 548

[56] References Cited

U.S. PATENT DOCUMENTS

| | | |
|---|---|---|
| 4,924,011 | 5/1990 | Denis et al. . |
| 4,924,012 | 5/1990 | Colin et al. . |
| 5,015,744 | 5/1991 | Holton . |
| 5,229,526 | 7/1993 | Holton . |
| 5,274,124 | 12/1993 | Holton . |
| 5,675,025 | 10/1997 | Sisti et al. . |
| 5,684,175 | 11/1997 | Sisti et al. . |
| 5,688,977 | 11/1997 | Sisti et al. . |
| 5,750,736 | 5/1998 | Sisti et al. . |
| 5,750,737 | 5/1998 | Sisti et al. . |
| 5,770,745 | 6/1998 | Swindell et al. . |

OTHER PUBLICATIONS

"Highly Efficient, Practical Approach to Natural Taxol", Denis et al, *Journal of the American Chemical Society*, p. 5917 (1988).

Greene and Gueritte–Voegelein, *J.Am. Chem. Socl.*, 1988, 110, 5917.

"A Chemoselective Approach to Functionalize the C–10 Position of 10–Deacetyl Baccatin III. Synthesis and Biological Properties of Novel Taxol Analogs", Kant et al., *Tetrahedron Letters*, vol. 35, No. 31, 1994, p. 5543.

*Primary Examiner*—Ba K. Trinh
*Attorney, Agent, or Firm*—Timothy J. Martin; Michael R. Henson; Mark H. Weygandt

[57] ABSTRACT

A chemic compound having the formula:

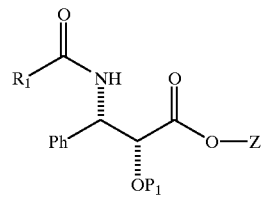

wherein $P_1$ is a hydroxyl protecting group, $R_1$ is an alkyl group, an olefinic group, an aromatic group, Ph, PhCH$_2$, an O-alkyl group, an O-olefinic group, an O-aromatic group, O—Ph, or O—CH$_2$Ph, and wherein Z is an N-imido group. In particular, $P_1$ may be selected from the group consisting of benzyl, benzyloxymethyl and benzoyl, and Z may be a heterocyclic N-imido group, preferably having 5 to 7 atoms in the ring and alternatively substituted with at least one electron withdrawing group, preferably selected from the group consisting of a chloro group, a fluoro group and a nitro group. In particular, it is contemplated that Z may be succinimido, phthalimido, 5-norbornene-2,3-dicarboxyimido, maleimido and substituted derivatives thereof.

34 Claims, No Drawings

C-2 HYDROXYL PROTECTED-N-ACYL (2R, 3S)-3-PHENYLISOSERINE N-IMIDO ACTIVATED ESTERS AND METHOD FOR PRODUCTION THEREOF

FIELD OF THE INVENTION

This invention generally relates to the synthesis of paclitaxel from precursor compounds. More particularly, though, this invention concerns the semi-synthesis of paclitaxel using a protected baccatin III backbone which is esterified with suitably protected side chain activated esters to produce an intermediate that may be converted to paclitaxel.

BACKGROUND OF THE INVENTION

The chemical compound referred to in the literature as taxol, and more recently "paclitaxel", has received increasing attention in the scientific and medical community due to its demonstration of anti-tumor activity. Paclitaxel has been approved for the chemotherapeutic treatment of several different varieties of tumors, and the clinical trials indicate that paclitaxel promises a broad range of potent anti-leukemic and tumor-inhibiting activity. As is known, paclitaxel is a naturally occurring taxane diterpenoid having the formula and numbering system as follows:

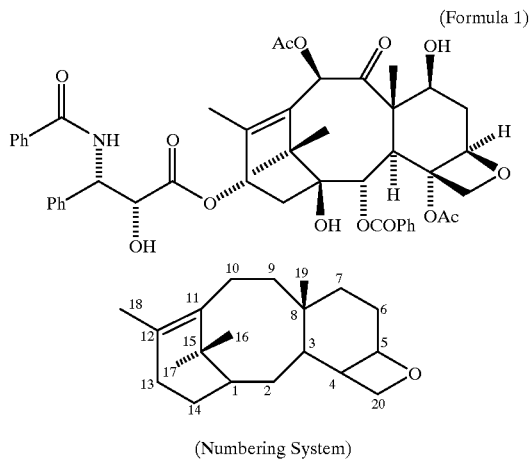

(Formula 1)

(Numbering System)

While the paclitaxel molecule is found in several species of yew (genus Taxus, family Taxaceae), the concentration of this compound is very low. Moreover, these evergreens are slow-growing. Thus, a danger exists that the increasing use of paclitaxel as an effective anti-cancer agent will deplete natural resources in the form of the yew trees. Indeed, while the bark of the yew trees typically exhibit the highest concentration of paclitaxel, the production of 1 kilogram of paclitaxel requires approximately 16,000 pounds of bark. Thus, the long term prospects for the availability of paclitaxel through isolation is discouraging.

The paclitaxel compound, of course, is built upon the baccatin III backbone, and there are a variety of other taxane compounds, such as baccatin III, cephalommanine, 10-deacetylbaccatin III, etc., some of which are more readily extracted in higher yields from the yew tree. Indeed, a relatively high concentration of 10-deacetylbaccatin III can be extracted from the leaves of the yew as a renewable resource. Typically, however, these other taxane compounds present in the yew tree do not exhibit the degree of anti-tumor activity shown by the paclitaxel compound.

Since the paclitaxel compound appears so promising as a chemotherapeutic agent, organic chemists have spent substantial time and resources in attempting to synthesize the paclitaxel molecule. A more promising route to the creation of significant quantities of the paclitaxel compound has been proposed by the semi-synthesis of paclitaxel by the attachment of the A-ring side chain to the C-13 position of the naturally occurring baccatin III backbone derived from the various taxanes present in the yew. See, Denis et al, a "Highly Efficient, Practical Approach to Natural Taxol", Journal of the American Chemical Society, page 5917 (1988). In this article, the partial synthesis of paclitaxel from 10-deacetylbaccatin III is described.

The most straightforward implementation of partial synthesis of paclitaxel requires convenient access to chiral, non-racemic side chains and derivatives, an abundant natural source of baccatin III or closely related diterpenoid substances, and an effective means of joining the two. Of particular interest then is the condensation of baccatin III or 10-deacetylbaccatin III with the paclitaxel A-ring side chain. However, the esterification of these two units is difficult because of the hindered C-13 hydroxyl of baccatin III located within the concave region of the hemispherical taxane skeleton. For example, Greene and Gueritte-Voegelein reported only a 50% conversion after 100 hours in one partial synthesis of paclitaxel. J. Am. Chem. Soc., 1988, 110, 5917.

In U.S. Pat. No. 4,929,011 issued May 8, 1990 to Denis et al entitled "Process for Preparing Taxol", the semi-synthesis of paclitaxel from the condensation of a (2R,3S) side chain acid of the general formula:

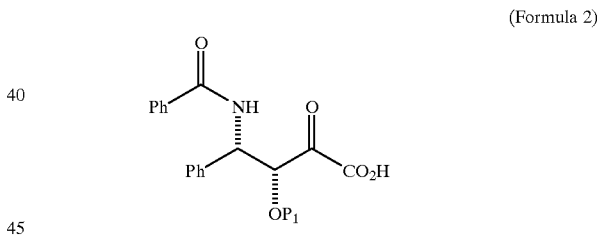

(Formula 2)

wherein $P_1$ is a hydroxy protecting group with a taxane derivative of the general formula of:

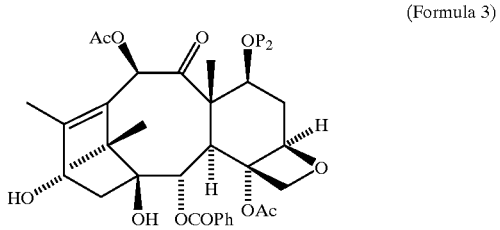

(Formula 3)

wherein $P_2$ is a hydroxy protecting group is described wherein the condensation product is subsequently processed to remove the $P_1$ and $P_2$ protecting groups. In Denis et al, the (2R, 3S) 3-phenylisoserine derivative, with the exception of the $P_1$ protecting group, is the A-ring side chain for the paclitaxel molecule. The $P_2$ protecting group on the baccatin III backbone is, for example, a trimethylsilyl or a trialkylsilyl radical.

An alternative semi-synthesis of paclitaxel is described in U.S. Pat. No. 5,770,745 to Swindell et al. Swindell et al. discloses semi-synthesis of paclitaxel from a baccatin III backbone by the condensation with a side chain having the general formula:

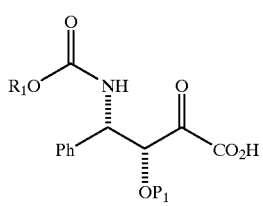

(Formula 4)

wherein $R_1$ is alkyl, olefinic or aromatic or $PhCH_2$ and $P_1$ is a hydroxyl protecting group.

The side chain in Swindell et al is distinct from the side chain attachment used in Denis et al, above, in that the nitrogen is protected as a carbamate. Preferably, the A-ring side chain is benzyloxycarbonyl (CBZ) protected. After esterification, the CBZ protecting group is removed and replaced by PhCO to lead to paclitaxel. This process generated higher yields than that described in Denis et al. In Swindell et al., the preferred masking groups were selected to be trichloroethoxymethyl or trichloroethoxycarbonyl. Benzyloxymethyl (BOM) was, however, disclosed as a possible side chain hydroxyl protecting group for the 3-phenylisoserine side chain, but, according to the processes described therein, the BOM protecting group could not be removed from the more encumbered C-2 hydroxyl in the attached 3-phenylisoserine side chain. The use of the BOM protected side chain was not extensively investigated, for this reason.

Subsequently, it has been shown (in U.S. Pat. No. 5,675,025 to Sisti et al., issued Oct. 7, 1997) that the BOM group could be removed from the more encumbered C-2 hydroxyl in the attached 3-phenylisoserine side chain.

U.S. Pat. No. 4,924,012, issued May 8, 1990 to Colin et al discloses a process for preparing derivatives of baccatin III and of 10-deacetylbaccatin III, by condensation of an acid with a derivative of a baccatin III or of 10-deacetylbaccatin III, with the subsequent removal of protecting groups by acid hydrolysis. Several syntheses of TAXOTERE®) (Registered to Rhone-Poulenc Sante) and related compounds have been reported in the *Journal of Organic Chemistry:* 1986, 51, 46; 1990, 55, 1957; 1991, 56, 1681; 1991, 56, 6939; 1992, 57, 4320; 1992, 57, 6387; and 993, 58, 255; also, U.S. Pat. No. 5,015,744 issued May 14, 1991 to Holton describes such a synthesis. Additional techniques for the synthesis of paclitaxel and paclitaxel analogues are discussed in U.S. Pat. No. 5,688,977 to Sisti et al., U.S. Pat. No. 5,750,737 to Sisti et al., U.S. Pat. No. 5,684,175 to Sisti et al. and U.S. Pat. No. 5,750,736 to Sisti.

Despite the advances made in the semi-synthesis of the paclitaxel molecule in the above described processes, there remains a need for more efficient protocols for the synthesis of paclitaxel in order to increase efficiencies in yields and production rates. There remains such a need for semi-synthesis that may be implemented into commercial processes. There is a further need for efficient protocols for the synthesis of paclitaxel analogs, intermediates and various A-ring side chain structures.

SUMMARY OF THE INVENTION

It is an object of the present invention to provide new C-2 hydroxyl protected-N-Acyl (2R,3S)-3-phenylisoserine activated esters and production processes therefore, that are useful in the semi- synthesis of paclitaxel.

Another object of the present invention is to provide a new and useful process for the production of an hydrogenatable benzyl-type protected side chain which may be readily attached to a protected baccatin III backbone during the semi-synthesis of paclitaxel.

Still a further object of the present invention is to provide N-CBZ protected C-2 hydroxyl-benzyl protected (2R,3S)-3-phenylisoserine activated esters and production methods therefor.

Still a further object of the present invention is to develop efficient cost effective processes for the production of N-CBZ protected C-2 hydroxyl-benzyl protected (2R,3S)-3-phenylisoserine activated esters.

According to the present invention, then, a chemical compound is provided having the formula:

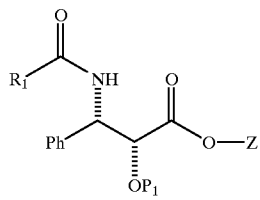

wherein $P_1$ is a hydroxyl protecting group, $R_1$ is an alkyl group, an olefinic group, an aromatic group, Ph, $PhCH_2$, an O-alkyl group, an O-olefinic group, an O-aromatic group, O—Ph, or O—$CH_2$Ph, and wherein Z is an N-imido group. In particular, $P_1$ may be selected from the group consisting of benzyl, benzyloxymethyl and benzoyl, and Z may be a heterocyclic N-imido group, preferably having 5 to 7 atoms in the ring and alternatively substituted with at least one electron withdrawing group, preferably selected from the group consisting of a chloro group, a fluoro group and a nitro group. In particular, it is contemplated that Z may be succinimido, phthalimido, 5-norbornene-2,3-dicarboxyimido, maleimido and substituted derivatives thereof.

The present invention is also directed to a chemical process useful in the production of paclitaxel, paclitaxel analogs and their intermediates. This process includes the step of reacting a (2R, 3S)-3-phenylisoserine derivative with N-hydroxy succinimide, or other N-hydroxy imide, in the presence of DCC or other carbodiimide to produce the activated esters. Alternatively, a suitable mixed anhydride of the acid may be formed and reacted with N-hydroxy succinimide, or other N-hydroxy imide, without a carbodiimide to produce the desired activated ester.

These and other objects of the present invention will become more readily appreciated and understood from a consideration of the following detailed description of the exemplary embodiments.

DETAILED DESCRIPTION OF THE EXEMPLARY EMBODIMENTS

The present disclosure is broadly directed to a chemical process for the efficient production of paclitaxel, intermediates and precursors therefor. More specifically, the present invention concerns the semi- synthesis of paclitaxel by esterifying suitably protected 3-phenylisoserine activated esters having protecting groups at C-2 to the C-13 hydroxyl of 7O-protected baccatin III. More particularly, the present invention preferably utilizes CBZ protection at the C-7 site of the baccatin III. The general process described herein involves the production of C-7 CBZ baccatin III, the production of a suitably protected 3-phenylisoserine activated ester having a suitable protecting group at C-2, the condensation of the two compounds, and the subsequent deprotection, acylation, deprotection of the condensation product to form paclitaxel.

A. Production of C7-CBZ Protected Baccatin III

According to the present invention, two alternative routes are described which appear in copending Application Serial No. 08/922,684, to Sisti et al., for producing C7-CBZ protected baccatin III. On one hand, baccatin III can be protected at the C-7 site to yield C-7 CBZ baccatin III. On the other hand, 10-deacetylbaccatin III (10-DAB) can be directly converted to C-7 CBZ baccatin III without going through a baccatin III intermediate. Production from baccatin III is advantageous for its yield and simplicity. The method using 10-deacetylbaccatin III has an advantage since 10-deacetylbaccatin III is much more naturally abundant, and thus less expensive, than baccatin III; however, this alternative method has a reduced yield.

Route 1

(Using baccatin III)

C-7 CBZ baccatin III has the formula:

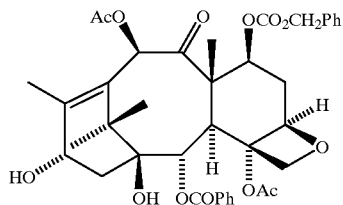

and can be synthesized from baccatin III according to the following reaction:

Reaction I

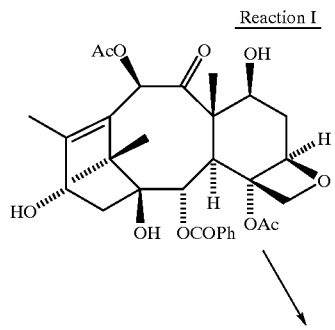

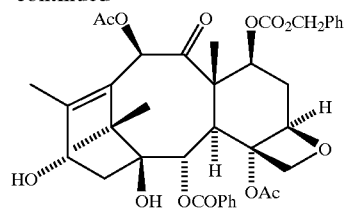

Baccatin III is dissolved in THF (tetrahydrofuran) to form a first solution, which is cooled under a nitrogen atmosphere to a reduced temperature of less than −20° C. n-Butyl lithium (1.6 M in hexane) is then added dropwise to the first solution to form a second solution, which is stirred for approximately five minutes at the reduced temperature. This creates the C-7 lithium alkoxide of baccatin III. Benzyl chloroformate (CBZ-Cl) is added dropwise to the second solution to form a third solution which is then stirred and allowed to warm to 0° C. over approximately one (1) hour. The third solution is quenched with cold saturated ammonium chloride to eliminate any excess n-butyl lithium and CBZ-Cl, and the mixture is concentrated under vacuum to yield a first residue. This first residue is next taken up in ethyl acetate and washed once with water to remove unwanted salts. Next, the organic layer is washed with brine. The organic layer is then dried and concentrated under vacuum to yield a second residue. The second residue is recrystallized or column chromatographed with ethyl acetate: hexane to give C-7 CBZ baccatin III as a white solid.

Instead of using n-butyl lithium, it should be appreciated that other alkali bases may be used, especially potassium hydride and sodium hydride, to form the C-7 metal alkoxide of baccatin III, to the extent understood by the ordinarily skilled artisan.

Route 2

(Using 10-deacetylbaccatin III)

Alternatively, C-7 CBZ baccatin III can be synthesized directly from 10-deacetylbaccatin III as follows:

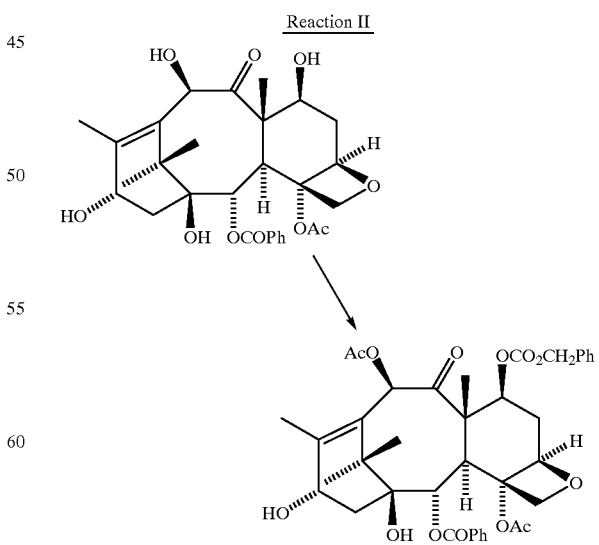

Reaction II

Here, 10-DAB III is dissolved in THF to form a first solution which is cooled to a reduced temperature of less than −20°

C., and preferably to −40° C., under a nitrogen atmosphere. At least two equivalents of n-butyl lithium (1.6 M in hexane) are then added dropwise to the first solution to form a second solution which is then stirred for approximately five minutes at the reduced temperature. Preferably, acetyl chloride (one equivalent) is added to the second solution to form a third solution which is stirred at the reduced temperature for approximately thirty minutes. Alternatively, acetic anhydride (one equivalent) may possibly be used in place of the acetyl chloride to acylate the 10-DAB III. In either case, benzyl chloroformate (one equivalent) is next added, and this fourth solution is stirred for an additional thirty minutes at the reduced temperature and then warmed to 0° C. over thirty minutes. The fourth solution is then quenched with cold saturated ammonium chloride at the reduced temperature to remove any excess n-butyl lithium, acetyl chloride and CBZ-Cl; this mixture is then warmed to room temperature. The solvent is removed under vacuum to yield an initial residue which is taken up in ethyl acetate and washed with water to remove unwanted salts. The organic layer is then washed with brine, dried and concentrated under vacuum to yield a final residue. The final residue is chromatographed (silica gel hexanes:ethyl acetate) to yield C-7 CBZ baccatin III. It is important to note that this method represents a direct synthesis of C-7 CBZ baccatin III from 10-DAB III, as the intermediate formed in this reaction is a C-7 lithium alkoxide of baccatin III, that is, the intermediate is not baccatin III itself.

While both Routes 1 and 2 specifically are directed to the production of derivatives of baccatin III, it should be apparent to the ordinarily skilled person that baccatin III analogs can be produced from the Route 2 process simply by substituting the appropriate acid chloride to the second solution in Route 2. This would result in the formation of analogues with different alkyl groups at C-10.

It should now be appreciated that both Route 1 and Route 2 to the production of C-7 CBZ baccatin III can be expressed as a generalized method. This method starts with a step of dissolving a starting compound selected from a group consisting of baccatin III and 10-deacetylbaccatin III in a first solvent to form a first solution. The first solution is then cooled to a temperature of −20° C. or less. Thereafter, an alkyl lithium base is added to the first solution thereby to form an intermediate compound having a lithium alkoxide at the C-7 position thereof. Next, as would be required for the 10-DAB III starting compound, the method includes selectively acylating, at the C-10 position, any of the first intermediate compound present in the first solution where the intermediate compound does not already have an acetyl group at the C-10 position thereby to produce a second solution of C-7 lithium alkoxide of baccatin III. Of course, where the starting compound is baccatin III, the C-10 position already has an acetyl group. In any event, the method includes a step of thereafter adding CBZ-Cl a to the second solution to form a third solution of C-7 CBZ baccatin III.

B. Production of N-Acyl C-2 Hydroxyl Protected (2R,3S)-3-Phenylisoserine A-Ring Side Chain Activated Esters The second precursor necessary for the semi-synthesis of paclitaxel according to the present invention is the N-acyl C-2 hydroxyl protected (2R,3S) phenylisoserine side chain activated ester having the general formula:

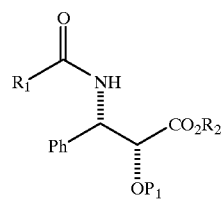

wherein $R_1$ is an alkyl group, an olefinic group, an aromatic group, Ph, PhCH$_2$, an O-alkyl group, an O-olefinic group, an O-aromatic group, O—Ph, or O—CH$_2$Ph. $P_1$ is a hydroxyl protecting group and $R_2$ can be an N-imido group or a phenyl ring substituted with one or more electron withdrawing groups. Imido groups contemplated by the present invention include such groups as succinimido, phthalimido, 5-norbornene-2,3-dicarboxyimido, or derivatives thereof such as a maleimido group or succinimido group substituted at the 3 and/or 4 positions, or other heterocyclic imido groups, preferably having 5 to 7 atoms in the ring, alternatively substituted with chloro, fluoro, nitro or other groups.

The preferred hydroxyl protecting group is a benzyloxymethyl (BOM) protecting group. Benzyl has also been demonstrated to be suitable as has benzoyl, and other protecting groups are believed suitable as well. The preferred N-Acyl group is benzyloxycarbonyl (CBZ). Other protecting groups and acyl groups (having alkyl, olefinic, and aromatic substituents and variations thereon) may be substituted, to the extent understood by the ordinarily skilled artisan.

The starting compound to produce the desired side chain is (2R,3S)-3-phenylisoserine ethyl ester to produce the preferred N-CBZ protected (2R,3S)-3-phenylisoserine ethyl ester according to the reaction:

Reaction III

Here, (2R,3S)-3-phenylisoserine ethyl ester was alternatively dissolved in either equal parts diethyl ether:water or equal parts methyl t-butyl ether:water and the solution was cooled to 0° C. The sodium carbonate was then added to the solution and benzylchloroformate was added dropwise over an interval of about five minutes and the resulting mixture stirred at 0° C. for approximately one hour. After the one hour stirring, the solution was then poured into water and extracted with methylene chloride or ethyl acetate, as desired. The organic layer is separated, dried and reduced under vacuum to residue. The residue was then recrystallized from ethyl acetate:hexane to result in N-CBZ (2R,3S)-3-phenylisoserine ethyl ester having the formula:

(Formula 5)

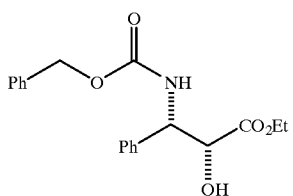

The N-CBZ (2R,3S)-3-phenylisoserine ethyl ester was next protected by the hydrogenatable benzyl-type protecting group, in several ways. For example, one route to the desired hydrogenatable benzyl protected side chain is as follows:

Reaction IV

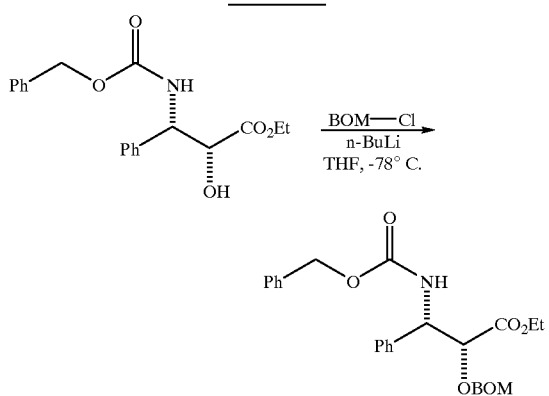

Here, the CBZ (2R,3S)-3-phenylisoserine ethyl ester is dissolved in anhydrous THF under a nitrogen atmosphere and cooled to a reduced temperature such as −40° C. or −78° C., for example, in a dry ice/acetone bath followed by the dropwise addition of an alkylithium agent, such as n-butyl lithium, although it is desirable that the alkylithium agent be a straight chain alkyl. In any event, the reaction is best done at a temperature no greater than 0° C. The resulting mixture was stirred for about ten minutes. Benzyloxymethyl chloride (BOM-Cl) was then added dropwise over an interval of about five minutes and the mixture stirred for approximately two to five hours at the reduced temperature. Thereafter, the solution was warmed to 0° C. and quenched with water. The resulting mixture is reduced under vacuum to residue, and this residue is thereafter taken up in ethyl acetate and washed with water and brine. The organic layer may then be dried and reduced under vacuum and the residue recrystallized from ethyl acetate:hexane or chromatographed with ethyl acetate:hexane to give the compound:

(Formula 6)

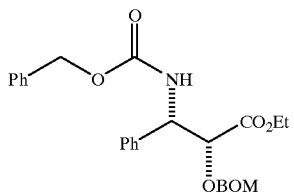

Another route in the production of the compound according to formula 6 is accomplished by dissolving the compound N-CBZ (2R,3S)-3-phenylisoserine ethyl ester in anhydrous methylene chloride. Thereafter, a tertiary amine base, such as diisopropylethylamine, is added along with BOM-Cl and the mix is refluxed for twenty-four hours. While this reaction route will produce N-CBZ, C-2 [hydroxyl] protected (2R, 3S)-3-phenylisoserine ethyl ester, the reaction proceeds much slower than the preferred route, discussed above.

In either instance, the resulting protected (2R,3S)-3-phenylisoserine ethyl ester compound of formula 6 may simply be converted to the N-CBZ C-2 O-BOM-protected (2R,3S) phenylisoserine intermediate by the reaction:

Reaction V

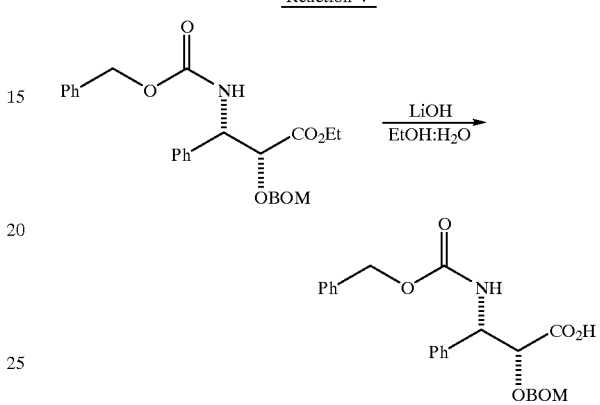

Here, the protected (2R,3S)-3-phenylisoserine ethyl ester is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1N HCl) and extracted with ethyl acetate. The resulting organic layer is separated, dried and reduced under vacuum. The residue acid is then isolated for use without further purification. This produces the desired side chain having the general formula:

(Formula 7)

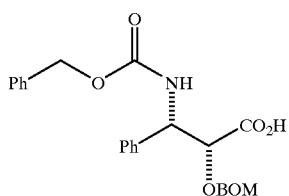

Benzyl itself is another example of a hydrogenatable benzyl protecting group that may be used instead of BOM. The compound of the formula:

(Formula 8)

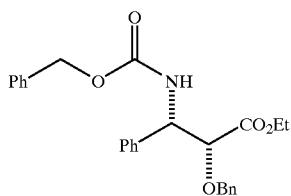

was therefore produced as above with the substitution of benzyl bromide for BOM-Cl in Reaction IV according to the reaction Reaction VI

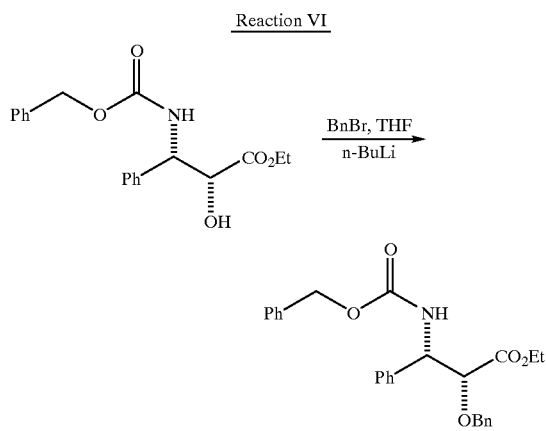

Here, the CBZ protected (2R,3S)-3-phenylisoserine ethyl ester is dissolved in anhydrous THF under a nitrogen atmosphere and cooled to a reduced temperature such as −40° C. or −78° C., for example, in a dry ice/acetone bath followed by the dropwise addition of an alkylithium agent, such as n-butyl lithium, although it is desirable that the alkylithium agent be a straight chain alkyl. The resulting mixture was stirred for about ten minutes. Benzyl bromide (BnBr) was then added dropwise over an interval of about five minutes and the mixture stirred for approximately two to five hours at the reduced temperature. Thereafter, the solution was warmed to 0° C. and quenched with water. The resulting mixture is reduced under vacuum to residue, and this residue is thereafter taken up in ethyl acetate and washed with water and brine. The organic layer may then be dried and reduced under vacuum and the residue recrystallized from ethyl acetate:hexane or chromatographed with ethyl acetate:hexane to give the compound of Formula 8.

Alternatively, the compound of Formula 8 may be obtained according to the reaction:

Reaction VII

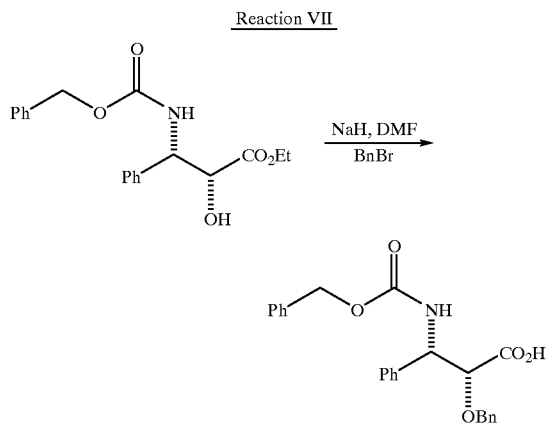

Here, to a stirred solution of NaH in anhydrous DMF under $N_2$ was added the compound of Formula 5 dissolved in DMF over five minutes. The mixture was then stirred at 0° C. for one half hour, after which time benzyl bromide (1.1 equivalents) was added dropwise over five minutes and the reaction stirred for two hours. The mixture was then quenched with $H_2O$. Thereafter, a selected one of diethyl ether and methyl t-butyl ether was added. The organic layer was then washed with four portions of $H_2O$, brine, and then dried and reduced under vacuum to produce the compound of Formula 8. Formula 8 may then be readily converted into:

(Formula 9)

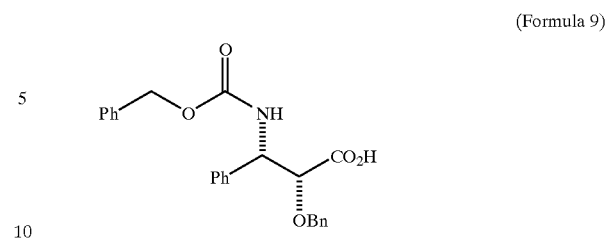

by the process of Reaction V, above.

N-CBZ C-2-OBOM protected (2R,3S)-3-phenylisoserine (Formula 7) may be converted into its corresponding activated esters by one of two routes, although it should be appreciated that other esterification methods known in scientific literature may be used to produce the activated ester, to the extent understood by the ordinarily skilled artisan. Further, it should be appreciated that the methods are applicable to C-2 and C-3N variations of Formula 7, to the extent understood by the ordinarily skilled artisan.

In the first route N-CBZ-C-2-OBOM protected (2R,3S)-3-phenylisoserine is mixed with 1.2 equivalents of dicyclohexylcarbodiimide or other suitable carbodiimide and 1.2 equivalents of either p-nitrophenol, pentaflurophenol, 2,4-dinitrophenol (or other substituted phenols, to the extent understood by the ordinarily skilled artisan) or N-hydroxy succinimide (or other N-hydroxy imides, to the extent understood by the ordinarily skilled artisan) in THF and stirred for several hours at room temperature. The preferred substituted phenol is p-nitrophenol. The preferred N-hydroxy imide is N-hydroxy succinimide. It should be appreciated that the substituted phenols and N-hydroxy imides contemplated by the present invention are either readily available or may be synthesized from readily available starting materials according to procedures known in the art.

The resulting mixture is diluted with ethyl acetate, cooled to 0° C. for several hours, stirred for an additional several minutes and filtered.

The filtrate is then washed with 1 N HCl, water, 20% aqueous $NaHCO_3$, water, brine, dried over sodium sulfate and reduced in vacuo to a residue. The residue may then be column chromatographed and/or recrystallized from ethyl acetate:heptane.

Exemplary reactions of the first route are as follows:

Reaction VIII (Formula 10)

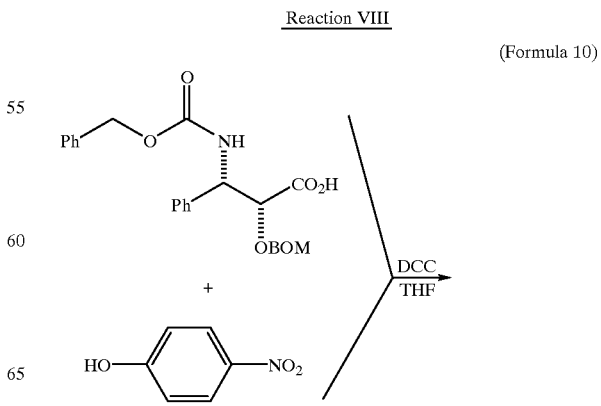

-continued

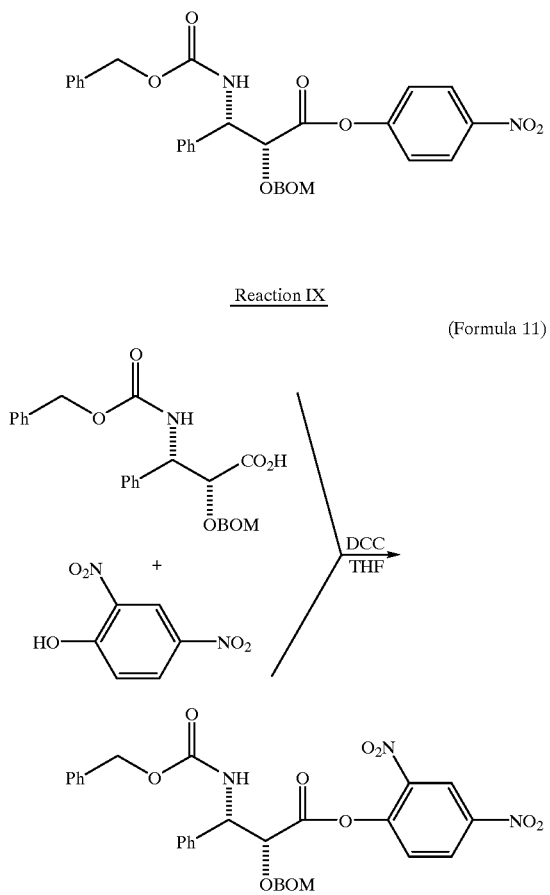

Reaction IX (Formula 11)

Reaction X (Formula 12)

Reaction XI (Formula 13)

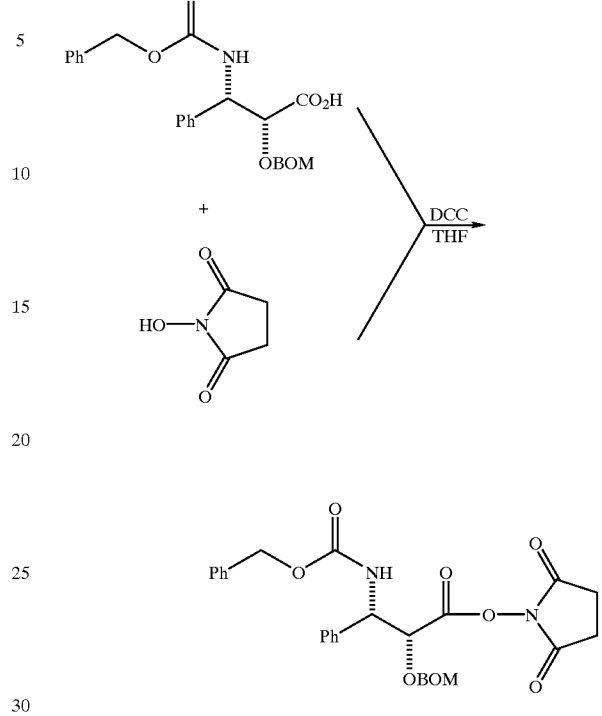

In the second route, a mixed anhydride of N-CBZ-C-2-OBOM 3-phenylisoserine may be reacted with either p-nitrophenol, pentaflurophenol, 2,4-dinitrophenol (or other substituted phenols, to the extent understood by the ordinarily skilled artisan) or N-hydroxy succinimide (or other N-hydroxy imides, to the extent understood by the ordinarily skilled artisan) to afford the corresponding activated esters. It is contemplated that mixed anhydrides having alkyl, olefinic, aromatic or other appropriate radicals might be used, to the extent understood by the ordinarily skilled artisan.

To a solution of N-CBZ-C-2-OBOM-3-phenylisoserine in THF cooled to −15° to −20° C. under nitrogen was added 1.5 equivalents of i-butyl chloroformate followed by 1.5 equivalents of N-methyl morpholine. The resulting mixture was stirred for several minutes followed by addition of 1.5 equivalents of either p-nitrophenol, pentaflurophenol, 2,4-dinitrophenol (or other substituted phenols, to the extent understood by the ordinarily skilled artisan) or N-hydroxy succinimide (or other N-hydroxy imides, to the extent understood by the ordinarily skilled artisan). The mixture was then stirred for several minutes between −15° to 0° C. then one hour at between 0° C. to 25° C. After which time the mixture was diluted with ethyl acetate, washed with water and brine, dried over sodium sulfate and reduced in vacuo to a residue. The residue was then purified by column chromatography and/or recrystallization from heptane:ethyl acetate.

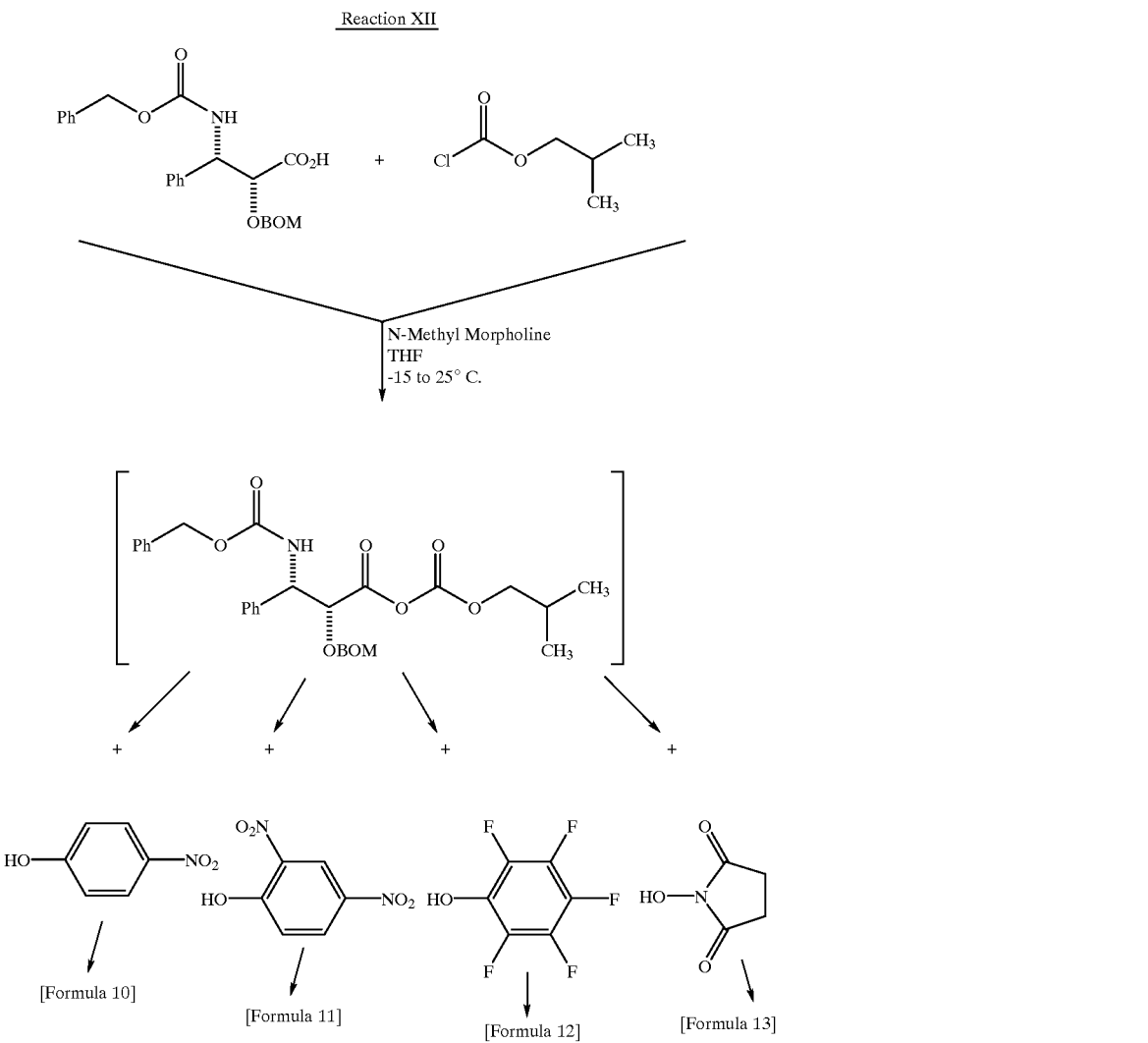

Reactions VIII, IX, X, XI and XII may be generalized by the following reactions XIII and XIV:

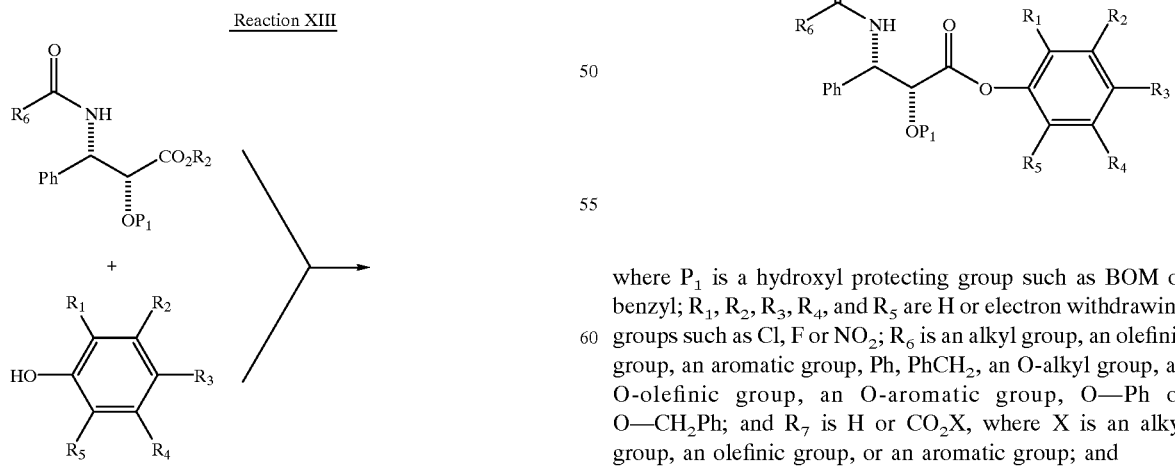

where $P_1$ is a hydroxyl protecting group such as BOM or benzyl; $R_1$, $R_2$, $R_3$, $R_4$, and $R_5$ are H or electron withdrawing groups such as Cl, F or $NO_2$; $R_6$ is an alkyl group, an olefinic group, an aromatic group, Ph, $PhCH_2$, an O-alkyl group, an O-olefinic group, an O-aromatic group, O—Ph or O—$CH_2Ph$; and $R_7$ is H or $CO_2X$, where X is an alkyl group, an olefinic group, or an aromatic group; and

Reaction XIV

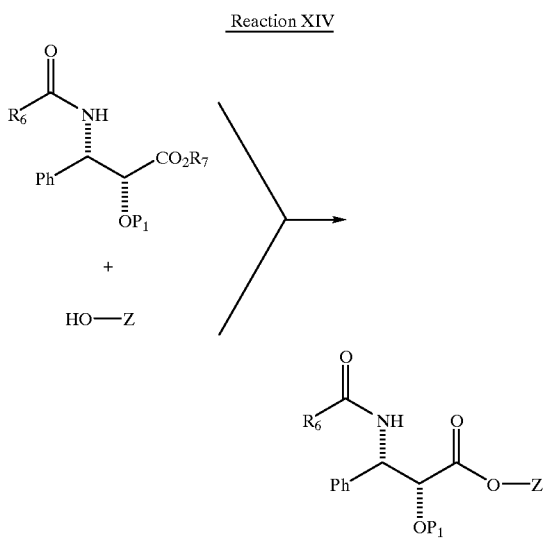

where $P_1$ is a hydroxyl protecting group such as BOM or benzyl; $R_1$ is an alkyl group, an olefinic group, an aromatic group, Ph, PhCH$_2$, an O-alkyl group, an O-olefinic group, an O-aromatic group, O—Ph or O——CH$_2$Ph; $R_2$ is H or CO$_2$X, where X is an alkyl group, an olefinic group, or an aromatic group; and Z is an N-imido group, including but not limited to succinimido, phthalimido, 5-norbornene-2,3-dicarboxyimido, or derivatives thereof such as a maleimido group or succinimido group substituted at the 3 and/or 4 positions, or other heterocyclic imido groups, preferably having 5 to 7 atoms in the ring, alternatively substituted with chloro, fluoro, nitro or other groups.

C. Condensation of C-7 CBZ Baccatin III with the Side Chain Activated Esters

The side chain activated esters (Formulas 10, 11, 12 or 13, or other variations to the extent understood by the ordinarily skilled artisan) as well as the C-7 CBZ baccatin III may now be condensed. This condensation may proceed in the presence of an appropriate lithium base (e.g., lithium hexamethyl disalizane or n-BuLi) in THF at 0° C. according to the reaction:

Reaction XV

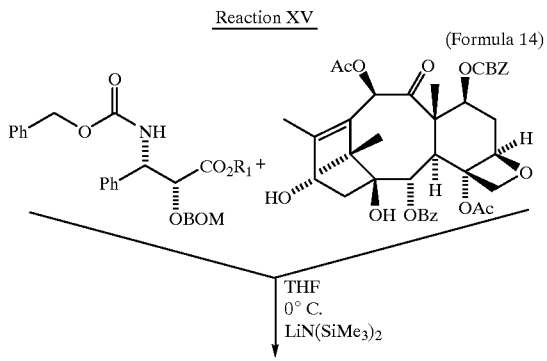

(Formula 14)

wherein R, is p-nitrophenyl (Formula 10), 2,4-dinitrophenyl (Formula 11), pentaflurophenyl (Formula 12), or other substituted phenyl groups, or N-succinimido (Formula 13), or other N-imido groups.

Here, C-7 CBZ baccatin III (1.0 equivalent) and the activated ester (Formula 10, 11, 12, 13 or others as discussed, 1.5 equivalents) are dissolved in anhydrous THF under nitrogen and brought to 0° C. It should be noted that other temperatures, including ambient temperature, have been shown to be suitable as well. To this is then added a suitable lithium base—in this case lithium hexamethyl disalizane, but n-butyl lithium can also be employed. This presumably generates the C-13 lithium alkoxide of C-7 CBZ baccatin III in analogous fashion to the C-13 lithium alkoxide of C-7 TES baccatin III as described by Holton (U.S. Pat. No. 5,229,526 and U.S. Pat. No. 5,274,124). The mixture is then stirred for a period of time, preferably several hours, although time periods as short as thirty minutes have been employed. The mixture is then diluted with a 1:1 mixture of ethyl acetate and 1N HCl, the organic phase collected and washed with water and brine, dried over sodium sulfate and reduced in vacuo to a residue. The residue could then be purified by column chromatography (ethyl acetate/heptane) or recrystallization (diethyl ether or methyl t-butyl ether or ethyl acetate/heptane) to afford the coupled product of Formula 14.

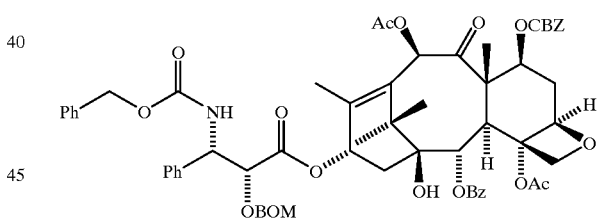

C-7 TES baccatin III can also be used in place of C-7-CBZ baccatin III to yield Formula 15.

(Formula 15)

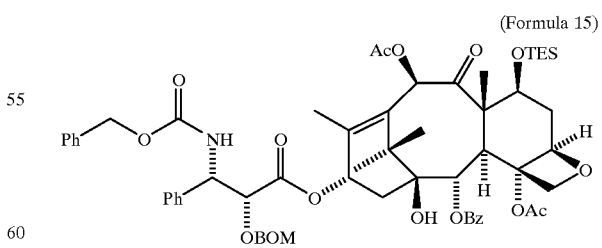

The synthesis of C-7 TES baccatin III has been described (see Denis et al in "A Highly Efficient, Practical Approach to Natural Taxol," *J. Am. Chem. Soc.,* 1988 p.5917 and Kant et al in "A Chemoselective Approach to Functionalize the C-10 Position of 10-deacetyl Baccatin III. Synthesis and Biological Properties of Novel Taxol Analogs", *Tetrahedron Letters*, Vol. 35, No. 31, 1994, p. 5543). Other C-7 protected baccatin III compounds may also be used, to the extent understood by the ordinarily skilled artisan.

The conversion of Formula 14 to paclitaxel has been previously described (Sisti et al, Ser. No. 08/719,488 now U.S. Pat. No. 5,750,737) and may be accomplished as follows:

D. Deprotections and Acylations to Form Paclitaxel from Formula 14

The compound according to Formula 14 may now be converted into paclitaxel by removing the nitrogen and C-7 CBZ groups, putting the benzoyl group onto the nitrogen, and finally removing the C-2' benzyl-type protecting group. Removal of the CBZ groups, and subsequent addition of the benzoyl group to the nitrogen are accomplished as follows (BOM is shown as the protecting group at the C-2' hydroxyl site, although benzyl could also be used):

Reaction XVI

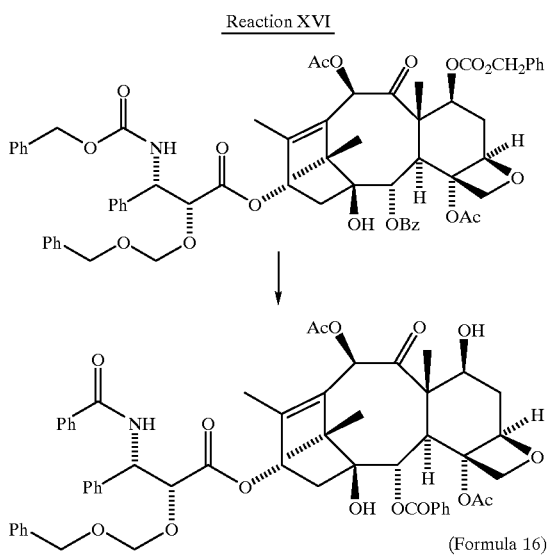

(Formula 16)

Here, the coupled product of Formula 14 is dissolved in isopropanol to which the Pearlman's catalyst is added. The resulting mixture is hydrogenated at 40 psi for twenty-four hours, although alternatively, the mixture can be stirred under one atmosphere of hydrogen for twenty-four hours. Alternatively, the mixture can be hydrogenated at 1 atm of hydrogen in the presence of at least one equivalent of tri-fluroacetic acid resulting in the TFA salt of the resultant amine. Thereafter, the mixture is filtered through diatomaceous earth and reduced under vacuum to residue. Preferably, the residue is taken up in toluene and anhydrous potassium carbonate added. Alternatively, the residue may be taken up in ethyl acetate or toluene and a tertiary amine base, such as triethylamine, is added. In either case, benzoyl chloride is then added dropwise, and the mixture stirred for two hours. The resulting mixture is then washed with water and finally brine. The resulting organic phase is then separated, dried, and concentrated under vacuum to yield C-2'-BOM paclitaxel (Formula 16).

Finally, the C-2'-BOM is removed according to the following reaction:

Reaction XVII

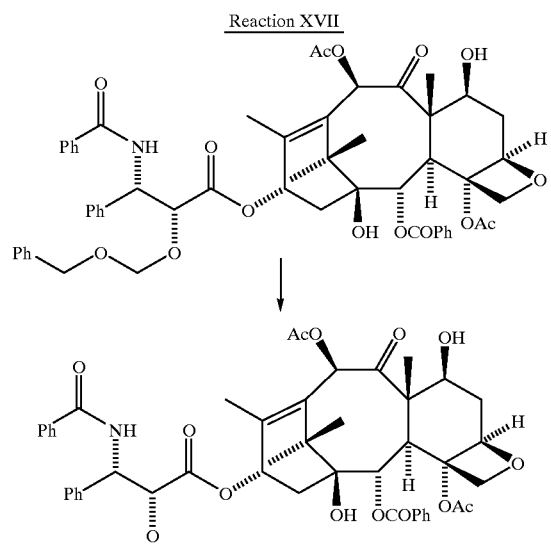

The BOM protected paclitaxel is dissolved in isopropanol to which Pearlman's catalyst is added. This mixture is hydrogenated for twenty-four hours under 40 psi hydrogen or twenty-four hours under one atmosphere of hydrogen in the presence of tri-fluoroacetic acid to yield paclitaxel.

The conversion of Formula 15 to paclitaxel has been previously described (Sisti et al, U.S. Pat. No. 5,675,025, Oct. 7, 1997) and may be accomplished as follows:

E. Deprotections and Acylation to Form Paclitaxel from Formula 15

The compound according to Formula 15 may now be converted into paclitaxel by removing the CBZ protecting group and acylating the side chain, removing the TES protecting group and removing the hydrogenatable benzyl protecting group. Here, several convenient routes have been found although in general, it is necessary to deprotect the C-7 site by removing the TES protecting group prior to deprotecting the C-2' site with the hydrogenatable benzyl protecting group. If the TES protecting group is not removed first, it is believed difficult at best to remove the hydrogenatable protecting group in a later processing step.

In any event, the preferred route of producing paclitaxel is to first remove the CBZ protecting group according to the reaction:

Reaction XVIII

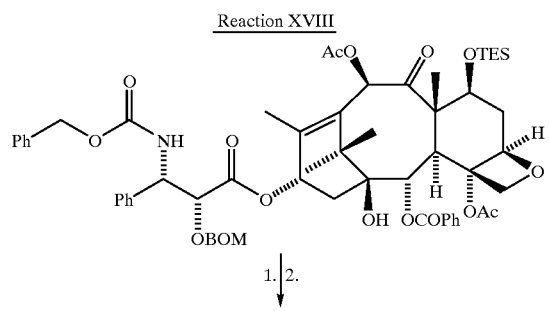

-continued

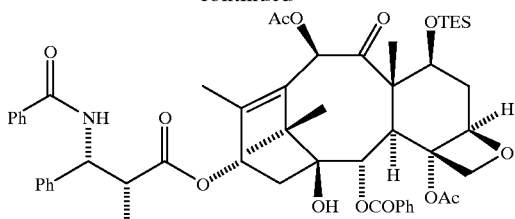

1. Pearlmans Cat., 1 Atm H₂, iPrOH
2. Benzoyl Chloride, EtOAc, TEA

Here, the coupled product of Formula 15 is dissolved in isopropanol to which the Pearlman's catalyst is added. The resulting mixture is stirred under one atmosphere of hydrogen for twenty-four hours. Thereafter, the mixture is filtered through diatomaceous earth and reduced under vacuum to residue. The residue may then be taken up in ethyl acetate or toluene and a tertiary amine base, such as triethylamine is added. Benzoyl chloride was added dropwise, and the mixture stirred for two hours. The resulting mixture was then washed with dilute aqueous solution of NaHCO₃, water, and finally brine. The resulting organic phase was then separated, dried and reduced under vacuum to yield the CBZ deprotected/acylated compound:

(Formula 17)

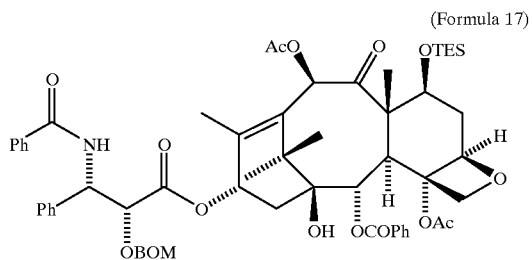

Next, the compound of Formula 17 is deprotected at C-7 according to the reaction:

Reaction XIX

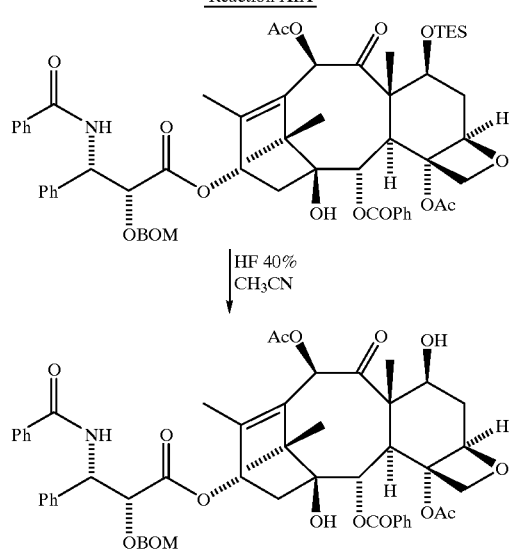

Here, the compound of Formula 17 was dissolved in acetonitrile (CH₃CN) at 0° C. Hydrofluoric acid (40% aqueous) was then added and the mixture stirred for ten hours while being held at 0° C. Thereafter, the mixture is diluted with ethyl acetate, saturated aqueous solution of NaHCO₃, water and finally brine. The organic phase was separated, dried and reduced under vacuum to produce a deprotected product at the C-7 position according to the formula:

(Formula 18)

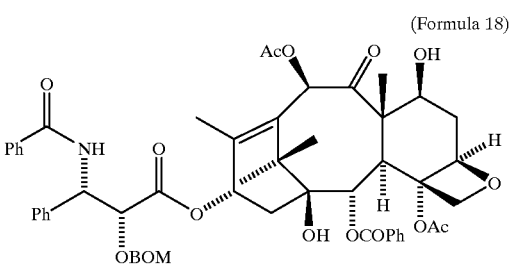

Finally, the compound of Formula 18 is deprotected at C-2' to remove the hydrogenatable benzyl-type (BOM) protecting group and to liberate the C-2' hydroxy group thereby resulting in the desired paclitaxel. This is accomplished according to the reaction:

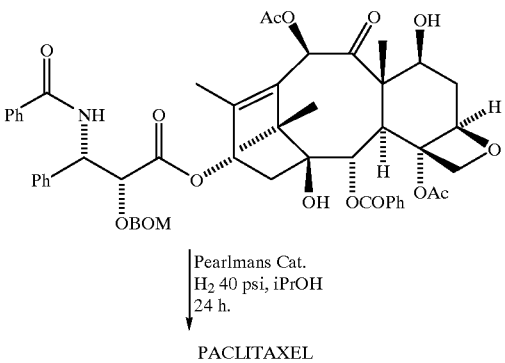

Pearlmans Cat.
H₂ 40 psi, iPrOH
24 h.

PACLITAXEL

Alternatively, the compound of Formula 15 may first be dissolved in CH₃CN at 0° C. and hydrofluoric acid (40% aqueous) added to deprotect the compound at the C-7 site by removing the TES protecting group. This results in a compound according to the Formula (Formula 19)

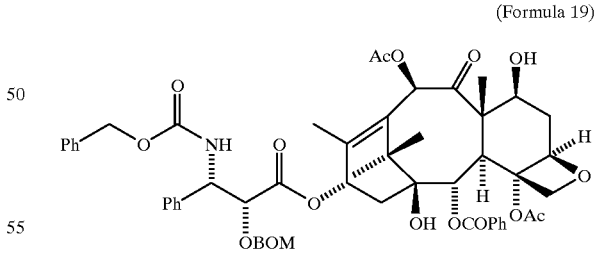

Next, the CBZ protecting group may be removed in a manner similar to that described above. Here, the compound of Formula 19 is dissolved in isopropanol and Peariman's catalyst was added along with trifluoroacetic acid (TFA) (one equivalent). The mixture was held at 40 psi of hydrogen at room temperature for approximately four days. This removes the CBZ protecting group and forms the C-2' BOM protected paclitaxel compound as a TFA salt. The mixture was filtered through diatomaceous earth and reduced under vacuum. Next, a base plus an acylating agent was added to the residue. Specifically, the TFA salt of the C-2' BOM protected compound was dissolved in pyridine and either benzoyl chloride or benzoic anhydride was added. The resulting product is:

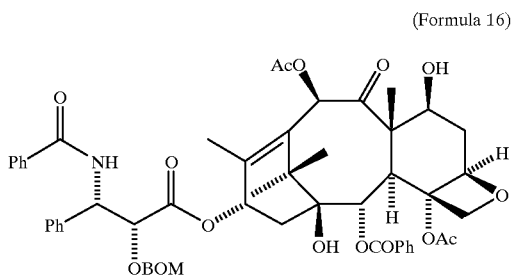

(Formula 16)

The compound of Formula 16 is dissolved in isopropyl alcohol and placed in a Parr bottle and Pearlman's catalyst was added. The mixture was hydrogenated for twenty-four hours at 40 psi of hydrogen. Thereafter, the mixture was filtered through diatomaceous earth and the eluent reduced under vacuum. The residue may then be column chromatographed according to any desired technique or recrystallized from ethyl acetate:hexane for the final paclitaxel product.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A chemical compound having the formula:

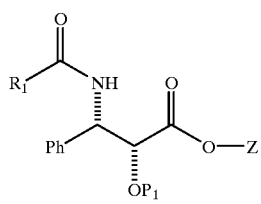

wherein $P_1$ is a hydroxyl protecting group, $R_1$ is an alkyl group, an olefinic group, an aromatic group, an O-alkyl group, an O-olefinic group, or an O-aromatic group, and wherein Z is an N-imido moiety.

2. A chemical compound according to claim 1 wherein $P_1$ is selected from the group consisting of benzyl, benzyloxymethyl and benzoyl.

3. A chemical compound according to claim 2 wherein $R_1$ is O—$CH_2$Ph.

4. A chemical compound according to claim 3 wherein $P_1$ is benzyloxymethyl.

5. A chemical compound according to claim 1 wherein Z is a heterocyclic N-imido moiety.

6. A chemical compound according to claim 5 wherein Z is a heterocyclic N-imido moiety having 5 to 7 atoms in the ring.

7. A chemical compound according to claim 5 wherein Z is a heterocyclic N-imido moiety substituted with at least one electron withdrawing group.

8. A chemical compound according to claim 7 wherein said electron withdrawing group is selected from the group consisting of a halogen and a nitro group.

9. A chemical compound according to claim 7 wherein said heterocyclic N-imido moiety is substituted with a plurality of electron withdrawing groups, wherein a first electron withdrawing group substituted on said heterocyclic N-imido moiety is of a type different from a second electron withdrawing group substituted on said heterocyclic N-imido moiety.

10. A chemical compound according to claim 1 wherein Z is selected from the group consisting of succinimido, phthalimido, 5-norbornene-2,3-dicarboxyimido, and maleimido moieties and substituted derivatives thereof.

11. A chemical compound selected from the group consisting of Formulas 1 to 5, as follows:

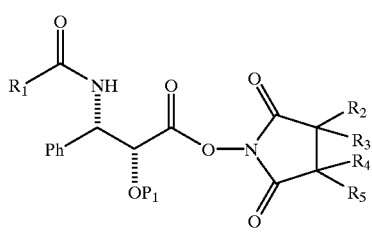

Formula 1

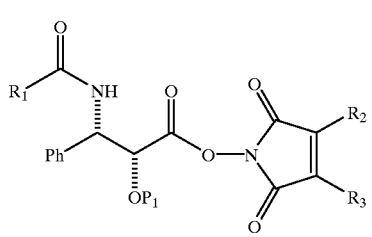

Formula 2

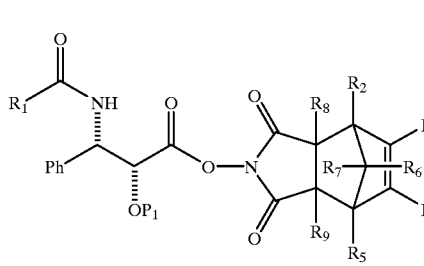

Formula 3

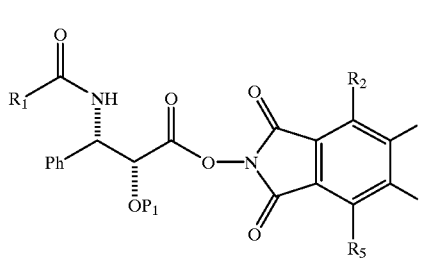

Formula 4

-continued

Formula 5

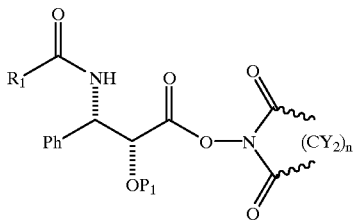

wherein $P_1$ is a hydroxyl protecting group; $R_1$ is an alkyl group, an olefinic group, an aromatic group, an O-alkyl group, an O-olefinic group, or an O-aromatic group; $R_{2-9}$ and Y are each selected from the group consisting of H and an electron withdrawing group; and n is an integer.

12. A chemical compound according to claim 11 wherein $P_1$ is selected from the group consisting of benzyl, benzyloxymethyl and benzoyl.

13. A chemical compound according to claim 12 wherein $R_1$ is O—$CH_2Ph$.

14. A chemical compound according to claim 11 wherein said chemical compound comprises Formula 5 wherein n has an integer value of 2 to 4.

15. A chemical compound according to claim 11 wherein said electron withdrawing group is selected from the group consisting of a halogen and a nitro group.

16. A chemical process to form an ester derivative useful in the production of paclitaxel, paclitaxel analogs and their intermediates comprising the step of reacting a first compound of the general formula:

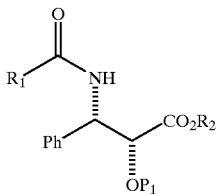

with a second compound of the general formula:

HO—Z to give an intermediate compound of the general formula:

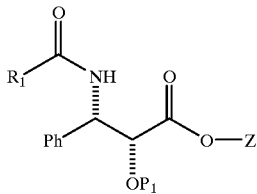

wherein $P_1$ is a hydroxyl protecting group; $R_1$ is an alkyl group, an olefinic group, an aromatic group, an O-alkyl group, an O-olefinic group, or an O-aromatic group, $R_2$ is H or $CO_2X$ where X is an alkyl group, an olefinic group or an aromatic group; and wherein Z is an N-imido moiety.

17. A chemical process according to claim 16 wherein $P_1$ is selected from the group consisting of benzyl, benzyloxymethyl and benzoyl.

18. A chemical process according to claim 16 wherein $R_2$ is H and the step of reacting is conducted in the presence of THF and a carbodiimide.

19. A chemical process according to claim 18 wherein the carbodiimide is dicyclohexylcarbodiimide.

20. A chemical process according to claim 16 wherein $R_2$ is $CO_2X$, where X is an alkyl group, an olefinic group, or an aromatic group.

21. A chemical process according to claim 20 wherein X is —$CH_2CH(CH_3)_2$.

22. A chemical process according to claim 20 wherein the step of reacting is conducted in the presence of N-methyl morpholine and THF.

23. A chemical process according to claim 20 wherein the first compound is formed by reacting a compound having the formula:

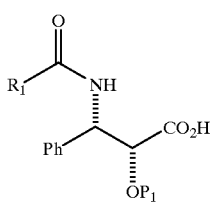

with a compound having the formula Cl—$CO_2X$ to give the first compound.

24. A chemical process according to claim 16 wherein $R_1$ is O—$CH_2Ph$.

25. A chemical process according to claim 16 wherein Z is a heterocyclic N-imido moiety.

26. A chemical process according to claim 25 wherein Z is a heterocyclic N-imido moiety having 5 to 7 atoms in the ring.

27. A chemical process according to claim 16 wherein Z is selected from the group consisting of succinimido, phthalimido, 5-norbornene-2,3-dicarboxyimido, and maleimido moieties and substituted derivatives thereof.

28. A chemical compound according to claim 1 wherein $R_1$ is selected from the group consisting of Ph, $PhCH_2$, O—Ph and O—$CH_2Ph$.

29. A chemical compound according to claim 8 wherein said halogen is selected from the group consisting of a chloro group, a fluoro group, a bromo group and an iodo group.

30. A chemical compound according to claim 8 wherein said halogen is selected from the group consisting of a chloro group and a fluoro group.

31. A chemical compound according to claim 11 wherein $R_1$ is selected from the group consisting of Ph, $PhCH_2$, O—Ph and O—$CH_2Ph$.

32. A chemical compound according to claim 15 wherein said halogen is selected from the group consisting of a chloro group, a fluoro group, a bromo group and an iodo group.

33. A chemical compound according to claim 15 wherein said halogen is selected from the group consisting of a chloro group and a fluoro group.

34. A chemical process according to claim 16 wherein $R_1$ is selected from the group consisting of Ph, $PhCH_2$, O—Ph and O—$CH_2Ph$.

* * * * *